United States Patent [19]

East et al.

[11] Patent Number: 4,861,331
[45] Date of Patent: Aug. 29, 1989

[54] IMPLANTABLE SHUNT SYSTEM AND METHOD OF ASSEMBLY

[75] Inventors: Gary P. East, Santa Barbara; Stephen W. Laguette; Alfons Heindl, both of Goleta; Leanne M. Lintula, Santa Barbara, all of Calif.

[73] Assignee: Pudenz-Schulte Medical Research Corp., Goleta, Calif.

[21] Appl. No.: 184,749

[22] Filed: Apr. 22, 1988

Related U.S. Application Data

[63] Continuation-in-part of Ser. No. 173,092, Mar. 24, 1988.

[51] Int. Cl.⁴ .............................................. A61M 5/00
[52] U.S. Cl. ...................................... 604/9; 604/247; 604/185; 137/854
[58] Field of Search .................... 604/8–10, 604/175, 185, 247; 137/854, 614.2; 285/332, 339

[56] References Cited

U.S. PATENT DOCUMENTS

| | | |
|---|---|---|
| 2,969,066 | 1/1961 | Holter et al. . |
| 3,020,913 | 2/1962 | Heyer . |
| 3,233,610 | 2/1966 | Wade . |
| 3,288,142 | 11/1966 | Hakim . |
| 3,452,757 | 7/1969 | Ames . |
| 3,527,226 | 9/1970 | Hakim . |
| 3,566,875 | 3/1971 | Stoehr . |
| 3,595,240 | 7/1971 | Mishler . |
| 3,654,932 | 4/1972 | Newkirk et al. . |
| 3,674,050 | 7/1972 | Kuffer et al. . |
| 3,683,929 | 8/1972 | Holter . |
| 3,690,323 | 9/1972 | Wortman et al. . |
| 3,758,073 | 9/1973 | Schulte . |
| 3,769,982 | 11/1973 | Schulte . |
| 3,827,439 | 8/1974 | Schulte et al. . |
| 3,886,948 | 6/1975 | Hakim . |
| 3,889,687 | 6/1975 | Harris et al. . |
| 3,924,635 | 12/1975 | Hakim . |
| 3,985,140 | 10/1976 | Harris . |
| 3,991,768 | 11/1976 | Portnoy . |
| 3,999,553 | 12/1976 | Spitz et al. . |
| 4,156,422 | 5/1979 | Hildebrandt et al. . |
| 4,190,040 | 2/1980 | Schulte . |

(List continued on next page.)

FOREIGN PATENT DOCUMENTS

| | | |
|---|---|---|
| 2444452 | 5/1975 | Fed. Rep. of Germany . |
| 1135947 | 1/1985 | U.S.S.R. . |

OTHER PUBLICATIONS

The Lancet, vol. 1.(64) 7326, p. 202; Jan. 25, 1964.
Surgical Forum, #, 1951, by Frank E. Nulsen, M.D. and Eugene B. Spitz, M.D., pp. 399–402.

*Primary Examiner*—Stephen C. Pellegrino
*Attorney, Agent, or Firm*—Kelly, Bauersfeld & Lowry

[57] ABSTRACT

A surgically implantable shunt system, including a flow control valve and an antechamber, is provided for controlling the release of entrapped body fluids. The flow control valve includes a pair of molded plastic bases situated, respectively, adjacent to an inlet and an outlet of the valve, which bases are situated within a flexible encasement. Each base includes an outer housing, a valve membrane carrier positioned within the housing, and a flow control member. The flow control members each include a rigid nail-like central support and a separate flexible resilient membrane positioned on the central support. A first flow control member is capable of selectively occluding the valve inlet, but is normally spaced from its base to permit free fluid flow through the inlet. The second flow control member is generally arch-shaped and resiliently biased to contact its respective base generally along the outer edge of the membrane in a manner permitting only controlled one-way flow through the valve. The antechamber permits injection of medication into the shunt between a proximal catheter and the distal flow control valve, and pumping of the medication in either direction. Additionally, a method for assembling the shunt system in a quick and economical manner is provided, which utilizes tapered grommets to anchor components in place prior to adhesively securing tubing to the flexible encasement.

44 Claims, 3 Drawing Sheets

U.S. PATENT DOCUMENTS

| | | |
|---|---|---|
| 4,215,695 | 8/1980 | Spitz et al. |
| 4,332,255 | 6/1982 | Hakim et al. |
| 4,387,715 | 6/1983 | Hakim et al. |
| 4,443,214 | 4/1984 | Marion |
| 4,464,168 | 8/1984 | Redmond et al. |
| 4,540,400 | 9/1985 | Hooven |
| 4,551,128 | 11/1985 | Hakim et al. |
| 4,552,553 | 11/1985 | Schulte et al. |
| 4,557,721 | 12/1985 | Hooven |
| 4,560,375 | 12/1985 | Schulte et al. |
| 4,578,057 | 3/1986 | Sussman |
| 4,583,967 | 4/1986 | Harris |
| 4,588,394 | 5/1986 | Schulte et al. |
| 4,595,390 | 6/1986 | Kakim et al. |
| 4,601,724 | 7/1986 | Hooven et al. |
| 4,605,395 | 8/1986 | Rose et al. |
| 4,627,832 | 12/1986 | Hooven et al. |
| 4,631,051 | 12/1986 | Harris |
| 4,636,194 | 1/1987 | Schulte et al. |
| 4,673,384 | 6/1987 | Marion |
| 4,675,003 | 6/1987 | Hooven |
| 4,676,772 | 6/1987 | Hooven |
| 4,681,559 | 7/1987 | Hooven |
| 4,749,003 | 6/1988 | Leason ............... 137/854 |
| 4,781,674 | 11/1984 | Redmond et al. ............ 604/9 |

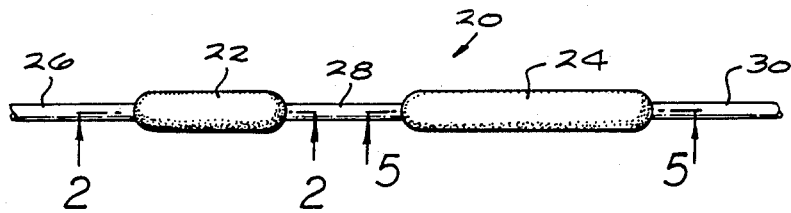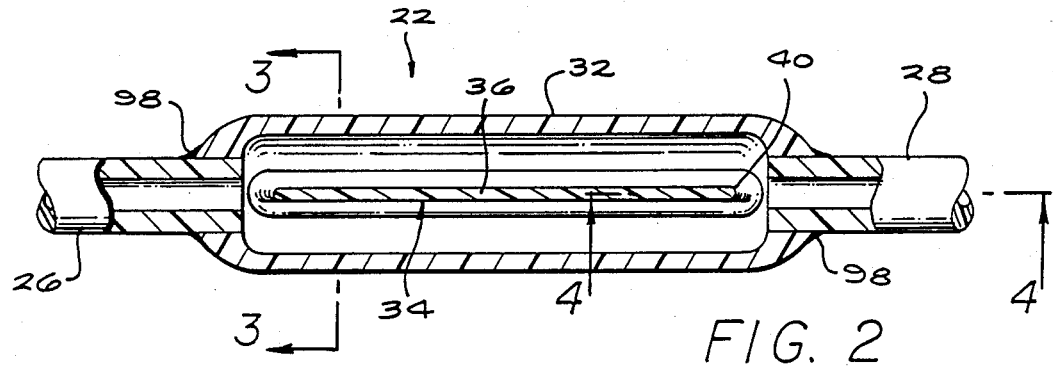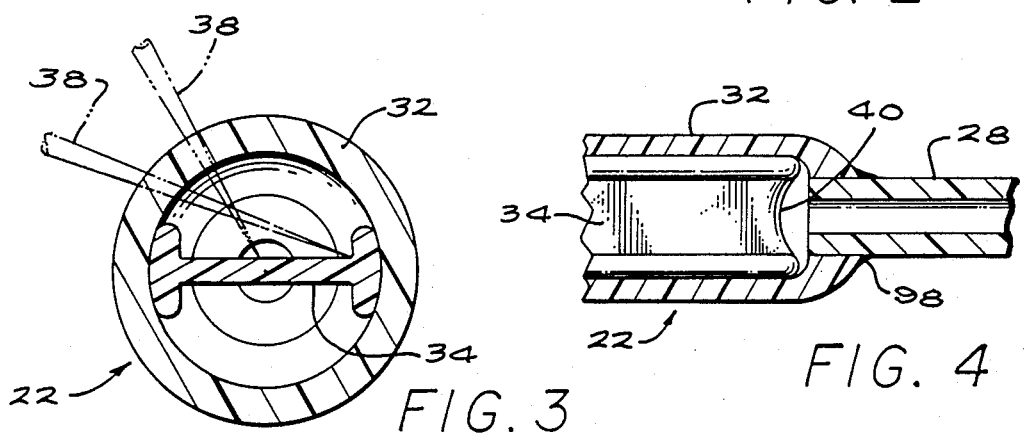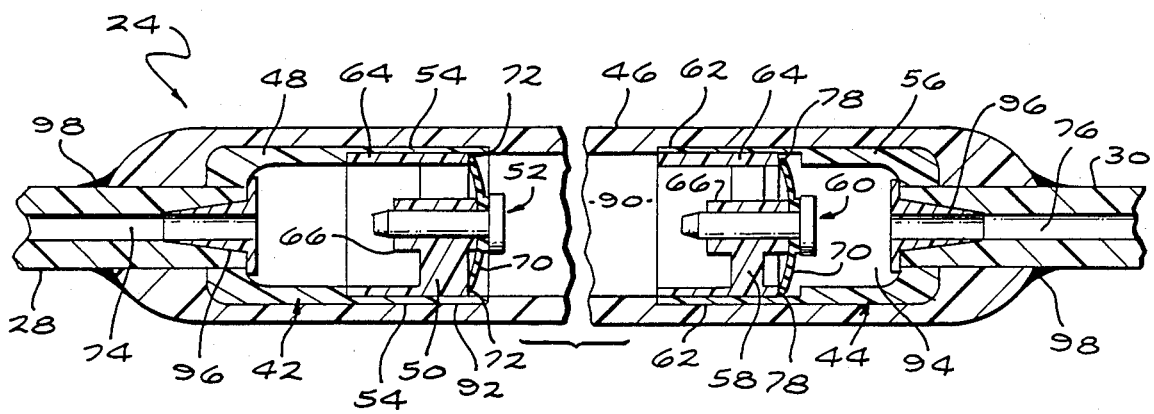

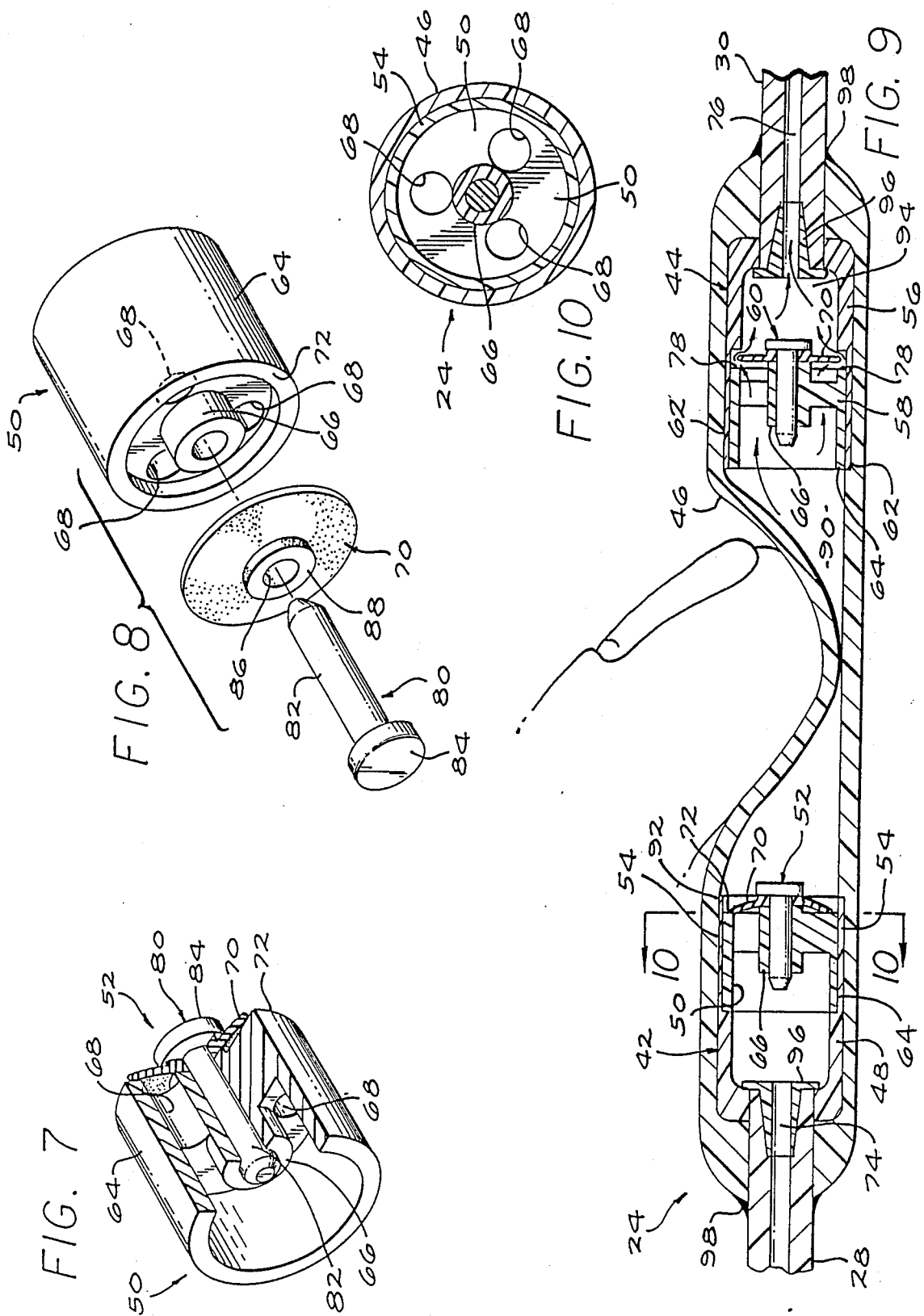

IMPLANTABLE SHUNT SYSTEM AND METHOD OF ASSEMBLY

RELATED APPLICATION

This is a continuation-in-part of U.S. patent application Ser. No. 173,092, filed Mar. 24, 1988 and entitled MULTIPLE-MEMBRANE FLOW CONTROL VALVE AND IMPLANTABLE SHUNT SYSTEM.

BACKGROUND OF THE INVENTION

This invention relates generally to surgically implanted shunt systems and related flow control valves. More particularly, this invention relates to shunt systems including one-way flow control valves for controlling the flow of cerebrospinal fluid out of a brain ventricle and preventing back flow of fluid into the brain ventricle.

As is well known in the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids which ought to drain away instead accumulate within the skull and thereby exert extreme pressure and skull deforming forces.

In treating hydrocephalus, cerebrospinal fluid accumulated in the brain ventricles is drained away by a catheter inserted into the ventricle through the skull, and the catheter is connected to a tube which conducts the fluid away from the brain to be reintroduced into the vascular system, as by extending through the patient's jugular vein to the atrium portion of the heart. To control the flow of cerebrospinal fluid and maintain the proper pressure in the brain ventricle, a pump or valve is placed in the conduit between the brain and the heart.

Many such devices have been previously used, but several of these devices have tended to become obstructed by particulate matter entering the drainage system or by the backward diffusion of blood into the system. Further, some prior devices have included moving parts which tended to adhere to other parts of the device and become immobile. When this occurs, the device itself becomes a barrier in the drainage system, and adds to the problem it is intended to solve.

Moreover, manufacturers have been faced with a dilemma regarding the use of metal components in such valves. Some prior devices have included metal components which tended to interfere with X-ray photography and produce radiation scatter ("sunburst effect") on films taken by computerized axial tomography (CAT) scanning equipment, and such X-ray photography and CAT scanning frequently accompanies the use of surgically implanted flow control valves.

It is often desirable to provide an antechamber as a component of a shunt system between the ventricular catheter and the flow control valve. Such placement of an antechamber as a component of the shunt system enables a physician to inject medication into the shunt system at a convenient location for flushing either distally or proximally. It has further been found desirable to provide a needle shield within the antechamber to provide means for detecting the location of the end of a needle inserted into the antechamber, and to further insure that the needle does not pass all the way through the antechamber where medication might be injected directly into the surrounding tissue. Although the benefits of a needle shield are self-evident, several problems have been encountered in prior devices. One problem relates to the unintended obstruction of the free flow of fluid from the ventricular catheter through the antechamber to the flow control valve. The positioning of a needle shield within an antechamber often presents the possibility that the antechamber can itself become occluded or become obstructed, and present a barrier in the drainage system. Another problem presented in prior antechambers is that after initial contact is made between the end of a needle and the needle shield, slight forces exerted on the needle may cause its tip to slide off the needle shield and, unknowingly, pass through the antechamber. This can lead to the injection of medication into the tissue surrounding the antechamber, rather than within the antechamber itself.

Further, in many instances it is believed to be desirable to reduce the size of the various shunt system components as much as possible without interfering with the desirable shunting and/or valving characteristics of the shunt system. With regard to the umbrella-type valve members illustrated in U.S. Pat. No. 4,560,375 (the contents of which are incorporated herein by reference), it has been found that the overall flexible nature of the elastomer materials comprising the flow control member effectively limits the smallest useful size of such members. In particular, during assembly of valves utilizing such umbrella-type members, the central support is pulled through an aperture in the base to position the resilient membrane with respect to one or more fluid flow apertures. As the size of the flow control member is reduced, and therefore the size of its central support, the inherent flexibility of the elastomer central support tends to make proper positioning of the resilient membrane very difficult. This difficulty arises from the fact that the central support undesirably stretches as it is being positioned within the base under most standard assembly procedures.

Accordingly, there has been a continuing need in the medical arts for convenient and effective devices for controlling the flow of fluid from one part of the human body to another, which devices are relatively inexpensive to manufacture and can be constructed substantially of nonmetallic parts which are not subject to adhering to one another and causing a malfunction of the device. Further, such a device is needed which utilizes multiple valve membranes in series for safety and reliability. Additionally a novel flow control member is needed which permits the economical manufacture and assembly of flow control valves on a smaller scale than that previously possible. Moreover, a shunt system is needed which includes an antechamber wherein medication can be injected between the ventricular catheter and the flow control valve, which antechamber provides means for effectively positioning the end of a needle within the injection chamber and yet is of such a construction that the unobstructed flow of fluid through the injection chamber is assured. As will become apparent from the following description, the present invention satisfies these needs and provides other related advantages.

SUMMARY OF THE INVENTION

The present invention resides in a shunt system for controlling the flow of fluids from one part of the human body to another, which is constructed substantially of nonmetallic materials and provides trouble-free and reliable operation in use. The system of the present invention is relatively inexpensive to manufacture, and can be easily modified to provide a variety of pressure/flow characteristics. In accordance with the present invention, the shunt system includes antechamber means for injecting medication into the shunt system, and a multiple-membrane flow control valve for controlling the flow of fluid from one portion of the human body to another.

In a preferred embodiment, the flow control valve includes a pair of relatively rigid bases which are invested within a relatively flexible encasement. Each base includes an outer housing and a valve membrane carrier securely positioned within the outer housing. The bases define inlet/outlet fluid passageways, and are positioned within the encasement such that the encasement defines an intermediate fluid passageway between the inlet/outlet fluid passageways. Further, the encasement is deformable by external pressure to facilitate manual flushing of the valve.

A flow control member is attached to each base to control the flow of fluid through the valve. Each flow control member includes a rigid central support or nail, and an arch-like flexible resilient membrane. The central support is attached to the respective valve membrane carrier and extends therefrom to support the resilient membrane over the outlet side of the valve membrane carrier. A first flow control member attached to the base adjacent the inlet is positioned with respect to a valve seat on the first base to normally permit free fluid flow through the inlet fluid passageway. It is further positioned, however, so that upon deformation of the encasement to flush the valve, the membrane temporarily contacts the adjacent valve seat in a manner to occlude the inlet fluid passageway. A second flow control member, on the other hand, is attached to the base adjacent the outlet. This second flow control member positions its resiliently biased membrane to contact a valve seat on the second base in a manner normally occluding the outlet fluid passageway, but selectively opens to permit controlled unidirectional flow therethrough. Such valve construction normally prevents flow of fluid through the valve, but permits fluid flow through the valve when the upstream fluid pressure exceeds the downstream fluid pressure by a predetermined amount.

Moreover, a variety of pressure/flow characteristics can be provided by the flow control valve of the present invention by providing it with different resilient membranes of varying thicknesses. The resistance to flow through the valve increases with an increase in membrane thickness.

In order to provide the desired resistance to adhesion between the bases and the resilient membranes, particularly during storage of the valve, the bases are preferably formed of polypropylene material and the membranes are preferably formed of a silicone elastomer material. Further, the flexible encasement which cooperates with the bases to form an intermediate fluid passageway is also preferably molded of a silicone elastomer material.

The base adjacent to the inlet preferably includes a relatively rigid recess in which the membrane is positioned to protect it against deformation when the flexible encasement is manually manipulated. With a similar purpose, the base adjacent the outlet includes a nondeformable outlet chamber in which the membrane is positioned. Further, the valve membrane carriers each define a plurality of fluid flow apertures or channels which are collectively covered by the adjacent flow control member.

The antechamber means includes, generally, a rigid needle shield situated within a relatively flexible encasement or housing. The structure of the antechamber means, and its position relative to a proximal catheter and the distal flow control valve, permits the injection of medication into the shunt system, and provides means for pumping the medication either distally or proximally. The needle shield has a dog bone-like cross-section, and the ends of the needle shield are contoured to permit its abutment against the antechamber encasement without occluding the openings therethrough. The dog bone-like cross-section of the needle shield helps to prevent a tip of a needle from slipping off the needle shield during injection of medication into the shunt system.

To facilitate assembly of the shunt system of the present invention, tubing is attached to each base by sliding an end of the tubing into the base, placing a grommet into the end of the tubing to expand the end thereof, and then pulling the tubing in a second direction away from the base. The expanded end of the tubing engages the base in a secure manner to form a frictional attachment. After the flexible encasement is placed over the bases, the open ends of the encasement are sealed to adjacent portions of the tubing extending outwardly from the valve.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective environmental view of the shunt system of the present invention, illustrating the relative positioning of an antechamber and a flow control valve;

FIG. 2 is an enlarged sectional view of the antechamber taken generally along the line 2—2 of FIG. 1;

FIG. 3 is an enlarged sectional view taken generally along the line 3—3 of FIG. 2, illustrating the specific construction of a needle shield within the antechamber;

FIG. 4 is a fragmented partially sectional view of the antechamber, taken generally along the line 4—4 of FIG. 2, illustrating the end configuration of the needle shield which is contoured to insure that the needle shield cannot occlude either the inlet or the outlet of the antechamber;

FIG. 5 is an enlarged sectional view of the flow control valve taken generally along the line 5—5 of FIG. 1;

FIG. 7 is an enlarged partially sectional view of a valve membrane carrier having a flow control member mounted thereon;

FIG. 8 is an exploded perspective view of the flow control member and valve membrane carrier illustrated in FIG. 7 and rotated 180°;

FIG. 9 is an enlarged sectional view of the flow control valve similar to that illustrated in FIG. 5, further showing one method of flushing the valve in the distal direction; and FIG. 10 is an enlarged elevational sectional view taken generally along the line 10—10 of FIG. 9.

DETAILED DESCRIPTION OF THE PREFERRED EMBODIMENT

Figure 6:
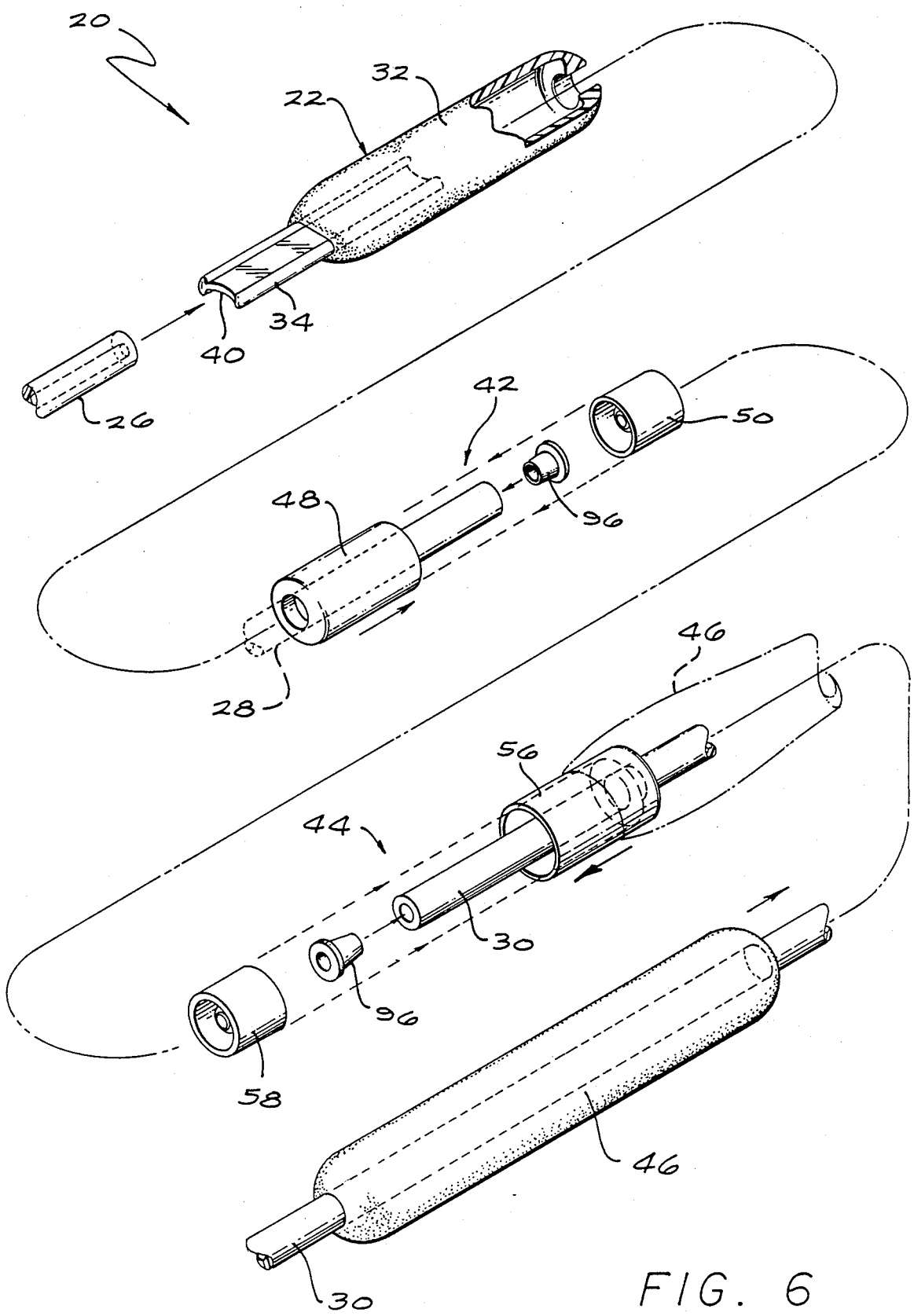
FIG. 6 is an exploded perspective view of the shunt system of the present invention, illustrating the manner in which various components are assembled.

As shown in the drawings for purposes of illustration, the present invention is concerned with a surgically implantable shunt system, generally designated in FIG. 1 by the reference number 20. This improved shunt system 20 includes, broadly, an antechamber 22 and a multiple-membrane flow control valve 24, which are connected by segments of surgical tubing 26, 28 and 30 to drain fluids from one portion of the human body to another. When the system 20 is used in the treatment of hydrocephalus, the antechamber 22 and the flow control valve 24 form portions of a fluid conduit extending from a proximal catheter (not shown), which is inserted through the skull into a brain ventricle containing cerebrospinal fluid under pressure, to a distal catheter (also not shown), which serves to discharge cerebrospinal fluid into, for example, the atrium portion of a patient's heart.

As will become apparent below, the shunt system of the present invention provides a highly reliable valve designed to prevent valve seat deformation and membrane to valve seat sticking. The shunt system of the present invention is inexpensive to produce, and the use of metal as a functional component has been eliminated. Moreover, positioning concerns relating to the valve have been minimized through the provision of a cylindrical design. Thus, due to the symmetry of the system, there is no top or bottom which must be anchored in place over the patient's skull for proper operation.

In accordance with the present invention, and as illustrated in FIGS. 1 through 4 and 6, the antechamber 22 includes a flexible, generally cylindrical encasement or housing 32 and a relatively rigid needle shield 34 positioned within the housing 32. The housing 32 includes openings at each end for receiving ends of tubing sections 26 and 28. The housing 32 is secured to the tubing sections 26 and 28 by a suitable adhesive. When connected as shown, fluid flowing through the shunt system 20 from the proximal catheter to the valve 24 must first pass through the antechamber 22.

The needle shield 34 is preferably constructed of a polypropylene material to form a plate 36 having a dog bone-like cross-section (see FIG. 3). A polypropylene material is preferred for the needle shield 34 in order to minimize any potential sticking between the housing 32, which is preferably constructed of a silicone elastomer material, and the needle shield. The dog bone-like cross-section of the needle shield 34 helps to prevent a tip of a needle 38 from slipping off the needle shield during injection of medication into the shunt system 20.

The needle shield 34 is further provided contoured ends 40, which permit the needle shield to abut adjacent the ends of the connecting tubing 26 and 28, without occluding them. This feature helps assure a user of the shunt system 20 that the flow of fluid through the components thereof will not be unintentionally obstructed.

As illustrated in FIG. 3, the housing 32 of the antechamber 22 can be punctured by the needle 38 in order to inject medication into the shunt system 20. The silicone elastomer material of the housing 32 has a sufficient thickness to permit insertion of a twenty-five gauge or smaller needle 38 without affecting the ability of the housing to reseal after needle has been withdrawn. The polypropylene material of the needle shield 34 has sufficient rigidity to prevent the needle 38 inserted through the housing 32 from passing all the way through the antechamber 22. This permits the physician to feel where the tip of the needle 38 is positioned during injection, to insure hat the medication is being injected into the shunt system 20 and not into the surrounding tissue. Following the injection of medication, the antechamber 22 can then be used as a pump for directing the medication toward the proximal catheter or toward the flow control valve 24.

To pump medication within the antechamber 22 toward the proximal catheter, the physician simply depresses the section of surgical tubing 28 between the antechamber 22 and the valve 24 through manual percutaneous pressure, and then depresses the housing 32 of the antechamber to flush the contents thereof through the proximal section of the surgical tubing 26. In a similar manner, the medication within the antechamber 22 can be pumped distally toward the valve 24. This is accomplished by percutaneously occluding the proximal surgical tubing 26, and then depressing the housing 32 to flush medication therein through the intermediate section of surgical tubing 28 to the valve 24.

With reference now to FIGS. 1 and 5 through 10, the flow control valve 24 includes a first base 42 positioned adjacent an inlet 74 of the valve, and a second base 44 positioned adjacent an outlet 76 of the valve. These bases 42 and 44 are invested within a flexible encasement 46.

The first base 42 includes a first outer housing 48, and a first valve membrane carrier 50 securely positioned within the first outer housing. The first valve membrane carrier 50 provides a cylindrical support for a first flow control member 52, and is press-fit within a support portion 54 provided by the first outer housing 48.

Similarly, the second base 44 includes a second outer housing 56, and a second valve membrane carrier 58 securely positioned within the second outer housing. The second valve membrane carrier 58 provides a cylindrical support for a second flow control member 60, and is press-fit within a support portion 62 provided by the second outer housing 56.

As shown best in FIGS. 7 and 8, each of the valve membrane carriers 50 and 58 include a cylindrical outer portion 64 which abuts against a correspondingly shaped inner surface of the support portions 54 and 62 to form a fluid tight seal therebetween. A central reinforced aperture 66 is provided for receiving a portion of the respective flow control member 52 or 60, and this central aperture 66 is surrounded by three additional apertures 68 which provide a plurality of channels through which fluid is permitted to flow.

The flow control members 52 and 60 are arranged serially within the valve 24 for controlling the flow of cerebrospinal fluid out of a brain ventricle and preventing backflow of fluid into the brain ventricle by the provision of resilient nonmetallic membranes 70 (see FIG. 8). The membranes 70 are molded of a synthetic polymer material different from the material of the valve membrane carriers 50 and 58, and are secured relative to the valve membrane carriers to generally cover the fluid flow apertures 68.

The first flow control member 52 is positioned on the first valve membrane carrier 50 to normally permit free fluid flow through the inlet fluid passageway. Thus, the first flow control member 52 does not, in the preferred embodiment, limit the flow of fluid from the valve inlet to the valve outlet. The first flow control member 52 is positioned, however, so that upon deformation of the encasement 46 to flush the valve 24, membrane 70 will temporarily sealingly contact a first valve seat 72 provided by the first valve membrane carrier 50, in a manner to occlude the inlet fluid passageway.

The resilient membrane 70 of the second flow control member 60, on the other hand, is normally biased to close communication between the inlet 74 and the outlet 76 of the valve 24, but will open to permit flow when the pressure on the proximal side of the resilient membrane 70 exceeds the pressure on the distal side by a predetermined amount. Moreover, should the pressure on the distal side of the resilient membrane 70 ever exceed the pressure on the proximal side, tending to cause flow in a reverse direction through the valve 24, the membrane 70 of the second flow control member 60 will seal tightly against a second valve seat 78 provided on the second valve membrane carrier 58. This effectively seals the fluid flow apertures 68 through the second valve membrane carrier 58, and prevents any such reverse flow through the valve 24.

The outer housings 48 and 56, and the valve membrane carriers 50 and 58 are preferably formed of a polypropylene material, and the membranes 70 are preferably formed of an elastomer material, preferably a silicone elastomer material. Both polypropylene and elastomer materials have been shown to produce an acceptable level of tissue reaction, and the use of this particular duality of materials, in contrast to the use of only a single material, markedly decreases the chance of the membranes 70 adhering to any portion of the bases 42 and 44, which would clog the drain passage and defeat the purpose of the valve 24.

An added advantage of using these particular materials is the avoidance of the negative effect of metal components, due to radiation scatter or "sunburst effect," on films taken by, for example, computerized axial tomography (CAT) scanning equipment. This type of scanning frequently accompanies the use of surgically implanted flow control valves, and the absence or limitation of metal in the area scanned will permit more accurate and complete results to be gathered from CAT scanning.

The flow control members 52 and 60 each include a rigid nail 80 having an elongated shaft 82 and an expanded head 84 at the end of the shaft. The nail 80 is capable of being driven into the central reinforced aperture 66 of the respective valve membrane carrier 50 and 58 to be frictionally retained therein. The nail is preferably constructed of polypropylene material which will not stretch or flex as the nail is being driven into the central reinforced aperture 66. After the nail is properly placed within the aperture, it is preferably heat welded to the respective valve membrane carrier 50 and 58.

The flexible resilient membranes 70 have an arch-shape, as for example a section of a sphere, and are designed to contact the valve seats 72 and 78 generally along the outer edges of the membrane in a manner surrounding the fluid flow apertures 68. Each membrane 70 is secured to its respective valve membrane carrier 50 and 58 by a central support/nail 80 described above. Each membrane 70 is provided an aperture 86 which is surrounded by a reinforced section 88. The shaft 82 extends through the membrane aperture 86 so that the reinforced section 88 abuts the head 84 of the nail 80. The membrane is retained in place on the nail 80 by an interference fit or by use of an adhesive, or by any other suitable means.

Since the valve 24 of the present invention is primarily designed to provide controlled resistance to cerebrospinal fluid flow from a brain ventricle to another location in the body, such as the atrium portion of the patient's heart, it will be appreciated that a doctor must be able to select a valve having the particular pressure/flow characteristics desired for each individual application. That is, a valve which permits flow at a relatively low pressure differential may not be suitable where the maintenance of a higher pressure differential is indicated. Toward this end, in order to provide a variety of valves having different pressure/flow characteristics, the valve 24 can be provided with thick membranes or relatively thin membranes. Resistance to flow increases with the increase in membrane thickness.

As illustrated best in FIGS. 5 and 9, the first and second bases 42 and 44 are separated from one another within the flexible encasement 46, so that the central section of the encasement can be deformed by external pressure to facilitate manual flushing of the valve 24. This central portion of the encasement 46 defines an intermediate fluid passageway 90 between the inlet fluid passageway provided through the first base 42, and the outlet fluid passageway provided through the second base 44.

In order to protect the resilient membranes 70 against possible deformation which may occur through the percutaneous manipulation of the valve 24, the first base 42 is provided a membrane shield 92 integrally formed with the first outer housing 48, which extends outwardly from the first valve seat 72. This membrane shield 92 forms a recess in which the first flow control member 52 is situated.

The second flow control member 60 is similarly protected against deformation due to percutaneous pressure, by situating the resilient membrane 70 thereof within an outlet chamber 94 provided between the second valve membrane carrier 58 and the valve outlet 76. The second flow control member 60 is thus completely surrounded by portions of the rigid second base 44, to completely protect it against deformation due to percutaneous manipulation of the flow control valve 24.

The method of assembling the shunt system 20 of the present invention will now be described with reference to FIG. 6. After the second flow control member 60 has been assembled to the second valve membrane carrier 58 so that the membrane 70 contacts the second valve seat 78 in a manner intended to normally occlude the outlet fluid passageway, but prior to assembling the second valve membrane carrier 58 to the second outer housing 56, an end of the third section of surgical tubing 30 is inserted through the second outer housing 56. A wedge-like grommet 96 is inserted into the end of the tubing 30. This causes the end of the tubing 30 to be expanded, so that as the tubing is withdrawn through the second outer housing 56, a friction interference fit is formed between the end of the tubing 30 and the second outer housing 56.

Similarly, an end of the second section of surgical tubing 28 is inserted through the first outer housing 48, and a grommet 96 is also placed within the end thereof. When this end of the second tubing section 28 is pulled back through the first outer housing 48, a friction interference fit is formed between that end of the second tubing section 28 and the first outer housing 48. Accordingly, it can be seen that the use of the grommets 96 permits the second and third tubing sections 28 and 30 to be anchored with respect to the first and second outer housings 48 and 56 of the first and second bases 42 and 44, in a quick and efficient manner prior to further assembly of the shunt system 20 and the valve 24.

Next, the first valve membrane carrier 50 (with the first flow control member 52 assembled thereto) is press-fit into the support portion 54 of the first outer housing 48. This completes assembly of the first base 42. The second valve membrane carrier 58 (with the second flow control member 60 properly fixed thereto) is press-fit into the support portion 62 of the second outer housing 56. This completes the assembly of the second base 44.

The flexible encasement 46 is then passed over the third section of tubing 30 and stretched over the first and second bases 42 and 44. When properly positioned, the first base 42 will abut against the inlet end of the encasement 46 with the second section of tubing 28 extending outwardly therefrom, and the second base 44 will abut against the outlet end of the encasement 46 with the third section of tubing 30 extending outwardly therefrom. The encasement 46 and the first and second bases 42 and 44 are finally fixed with respect to one another by the application of an adhesive 98 between the ends of the encasement and the outwardly extending sections of tubing 28 and 30.

Following insertion of the needle shield 34 into the antechamber housing 32, a second end of the second section of tubing 28 can be adhesively secured to the antechamber housing 32 in a conventional manner. Similarly, the first section of tubing 26 can be secured in a conventional manner to the other end of the antechamber housing 32.

To flush the flow control valve 24, the intermediate portion of the flexible encasement 46 is pressed downwardly (as shown by a finger in FIG. 9) to force fluid within the intermediate fluid passageway 90 through the fluid flow apertures 68 of the second valve membrane carrier 58, and past the second flow control member 60 to the valve outlet 76. The first flow control member 52 is positioned with respect to the first valve seat 72 so that upon an increase in pressure within the intermediate fluid passageway 90 with respect to downstream fluid pressure, the membrane 70 will seal against the first valve seat 72 and prevent retrograde flow out of the valve 24. Upon withdrawal of the percutaneous pressure from the flexible encasement 46, the second flow control member 60 will again engage the second valve seat 78 of the second valve membrane carrier 58 to altogether prevent the reverse flow of fluid through the fluid flow apertures 68, and therefore the entire valve 24.

From the foregoing it will be appreciated that the shunt system of the present invention provides a device by which the flow of cerebrospinal fluid out of a brain ventricle can be controlled while preventing the backflow of fluid into the brain ventricle, and by which the chance of a valve clogging the drain passage can be greatly decreased. The antechamber 22 and the valve 24 can be fabricated conveniently and economically, are trouble-free and reliable in use, provide convenient flushing of the shunt system, and can be easily adapted to provide a variety of pressure/flow characteristics. Although two flow control members are provided within the valve 24, only the second flow control member 60 controls the flow of fluid from the ventricular catheter through the shunt system 20. The first flow control member 52 is provided, primarily, to permit the intermediate fluid passageway 90 to be flushed as percutaneous pressure is applied to the flexible encasement 46. The provision of flow control members 52 and 60 utilizing a rigid central support or nail 80, avoids the difficulties inherent in utilizing similar umbrella-type valves having a flexible central support. This permits the size of the valve 24 to be sharply reduced, since the size of the membranes 70 and the overall flow control members can likewise be reduced. Moreover, the antechamber 22 includes features which help insure proper positioning of a needle within the antechamber for the injection of medication, yet the structure of the needle shield 34 is such that possible occlusion of the antechamber is minimized.

Although a particular embodiment of the invention has been described in detail for purposes of illustration, various modifications may be made without departing from the spirit and scope of the invention. Accordingly, the invention is not to be limited, except as by the appended claims.

We claim:

1. A surgically implantable shunt system, comprising:
an inlet;
an outlet;
a first base adjacent to the inlet, the first base including an inlet fluid passageway therethrough and a first valve seat surrounding a portion of the inlet fluid passageway;
a first flow control member attached to the first base and being positioned with respect to the first valve seat to normally permit free fluid flow through the inlet fluid passageway, and alternately, to selectively contact the first valve seat in a manner to occlude the inlet fluid passageway;
a second base adjacent to the outlet, the second base including an outlet fluid passageway therethrough and a second valve seat surrounding a portion of the outlet fluid passageway; and
a second flow control member attached to the second base so that the second flow control member contacts the second valve seat in a manner normally occluding the outlet fluid passageway but selectively opening to permit controlled unidirectional flow therethrough.

2. A shunt system as set forth in claim 1, including an intermediate fluid passageway between the inlet and outlet fluid passageways, and means for flushing fluid from the intermediate fluid passageway through the outlet fluid passageway by application of percutaneous manual pressure to the shunt system.

3. A shunt system as set forth in claim 2, wherein the flushing means comprises a flexible encasement generally surrounding the first and second bases, wherein the encasement is deformable by external pressure to facilitate manual flushing of the valve and defines the intermediate fluid passageway, and further wherein deformation of the flexible encasement causes the first flow control member to temporarily engage the first valve seat and occlude the inlet fluid passageway.

4. A shunt system as set forth in claim 1, wherein each flow control member includes a central support and a resilient membrane, the central support being attached to the respective base and extending therefrom to support the resilient membrane, the resilient membrane being generally arch-shaped and having a portion thereof capable of engaging the respective valve seat to occlude the respective fluid passageway.

5. A shunt system as set forth in claim 4, wherein each central support comprises a rigid nail which is anchored to its respective base, and wherein each resilient membrane comprises a flexible valve seat-engaging member.

6. A shunt system as set forth in claim 5, wherein the central support is formed of a polypropylene material, and the membrane is formed of an elastomer material.

7. A shunt system as set forth in claim 4, wherein the first base includes a first outer housing and a first valve membrane carrier securely positioned within the first outer housing, the first valve membrane carrier including means for positioning the central support of the first flow control member.

8. A shunt system as set forth in claim 7, wherein the first base includes a rigid recess in which the resilient membrane of the first flow control member is positioned.

9. A shunt system as set forth in claim 4, wherein the second base includes a rigid second outer housing and a second valve membrane carrier securely positioned within the second outer housing, the second valve membrane carrier including means for positioning the central support of the second flow control member so that the outer edges of the second resilient membrane contact the second valve seat.

10. A shunt system as set forth in claim 9, wherein the second outer housing forms an outlet chamber between the second valve membrane carrier and the outlet, and wherein the second resilient membrane is positioned within the outlet chamber.

11. A shunt system as set forth in claim 9, wherein the second valve membrane carrier defines a plurality of channels comprising a part of the outlet fluid passageway, and wherein the second valve seat is situated on the second valve membrane carrier.

12. A shunt system as set forth in claim 1, including means for injecting medication into the shunt system, the injecting means including an antechamber having an inlet, an outlet, a flexible encasement which defines an injection chamber, and a rigid needle shield situated within the injection chamber, the needle shield extending generally the length of the injection chamber and including needle stop means for preventing a tip of a needle from inadvertently slipping off the needle shield during injection of medication into the injection chamber, and means for preventing occlusion of the antechamber inlet and outlet by the needle shield, and further including tubing means for connecting the antechamber outlet with the first base.

13. A shunt system as set forth in claim 12, including grommet means for non-adhesively attaching an end of the tubing means to the first base.

14. A shunt system as set forth in claim 1, including distal tubing means for channeling fluid from the outlet, the distal tubing means being attached to the second base by grommet means for forming a non-adhesive attachment between the second base and the distal tubing means.

15. An implantable flow control valve for controlling the flow of fluid from one portion of the human body to another, said valve comprising:
an inlet;
an outlet;
a first base adjacent to the inlet and including a first outer housing and a first valve membrane carrier securely positioned within the first outer housing, the first outer housing and the first valve membrane carrier defining an inlet fluid passageway and a first valve seat surrounding a portion of the inlet fluid passageway;
a second base adjacent to the outlet and including a second outer housing and a second valve membrane carrier securely positioned within the second outer housing, the second outer housing and the second valve membrane carrier defining an outlet fluid passageway and a second valve seat surrounding a portion of the outlet fluid passageway, wherein the second outer housing forms an outlet chamber;
a flexible encasement generally surrounding the first and second bases, wherein the encasement is deformable by external pressure to facilitate manual flushing of the valve, the flexible encasement defining an intermediate fluid passageway between the inlet and outlet fluid passageways;
a first flow control member including a first rigid central support and a first arch-like flexible resilient membrane, the first central support being attached to the first valve membrane carrier and extending therefrom to support the first resilient membrane with respect to the first valve seat to normally permit free fluid flow through the inlet fluid passageway, the first resilient membrane further being positioned so that upon deformation of the encasement to flush the valve, the membrane temporarily contacts the first valve seat in a manner to occlude the inlet fluid passageway; and
a second flow control member including a second rigid central support and a second arch-like resilient membrane, the second central support being attached to the second valve membrane carrier and extending therefrom to support the second resilient membrane adjacent to the second valve seat, the second resilient membrane being resiliently biased to contact the second valve seat in a manner normally occluding the outlet fluid passageway but selectively opening to permit controlled unidirectional flow therethrough.

16. A valve as set forth in claim 15, wherein the first valve membrane carrier defines a plurality of channels comprising at least a part of the inlet fluid passageway, wherein the channels are collectively occluded in a controlled manner upon engagement by the first resilient membrane of the first valve seat.

17. A valve as set forth in claim 15, wherein the second valve membrane carrier defines a plurality of channels comprising at least part of the outlet fluid passageway, wherein the channels are collectively occluded in a controlled manner by the second flow control member.

18. A valve as set forth in claim 15, wherein the first base includes a rigid recess in which the first resilient membrane is positioned.

19. A valve as set forth in claim 15, wherein the second base provides a non-deformable outlet chamber, and wherein the second resilient membrane is positioned within the outlet chamber.

20. A valve as set forth in claim 15, including grommet means for non-adhesively attaching the bases to tubing means for channeling fluids to the inlet and from the outlet.

21. A surgically implantable fluid shunt, comprising:
an inlet;
an outlet;
a rigid base which resists deformation, the base having an inlet surface in communication with the inlet and an outlet surface in communication with the outlet;

an aperture through the base for permitting flow of fluid through the shunt from the inlet to the outlet; and a flow control member for controlling the flow of fluid from the inlet to the outlet, the flow control member including a rigid nail and an arch-like flexible resilient membrane fixed to the nail, wherein the nail is attached to the base adjacent to the aperture and extends therefrom to position the resilient membrane with a concave side thereof in facing relation with the inlet, the resilient membrane being resiliently biased such that outermost edges of the membrane contact the base in a manner normally preventing fluid flow through the shunt, the membrane selectively opening to permit controlled unidirectional flow through the shunt from the inlet to the outlet.

22. A shunt as set forth in claim 21, wherein the resilient membrane contacts the outlet side of the base in a manner surrounding the aperture to form a releasable seal between the outlet side of the base and the outermost edges of the membrane.

23. A shunt as set forth in claim 21 wherein the base is situated adjacent to the outlet and includes an outer housing and a valve membrane carrier securely positioned within the outer housing, the outer housing and the valve membrane carrier defining an outlet fluid passageway and a valve seat surrounding a portion of the outlet fluid passageway.

24. A shunt as set forth in claim 23, wherein the base forms a non-deformable outlet chamber, and wherein the flow control member is situated within the outlet chamber.

25. A shunt as set forth in claim 23, including a secondary base situated adjacent to the inlet and including a secondary outer housing and a secondary valve membrane carrier securely positioned within the secondary outer housing, the secondary outer housing and the secondary valve membrane carrier defining an inlet fluid passageway and a secondary valve seat surrounding a portion of the inlet fluid passageway.

26. A shunt as set forth in claim 25, including a flexible encasement generally surrounding the bases, wherein the encasement is deformable by external pressure to facilitate manual flushing of the shunt, the flexible encasement defining an intermediate fluid passageway between the inlet and outlet fluid passageways.

27. A shunt as set forth in claim 26, including a secondary flow control member including a rigid central support and an arch-like flexible resilient membrane, the central support being attached to the secondary valve membrane carrier and extending therefrom to support the resilient membrane with respect to the secondary valve seat to normally permit free fluid flow through the inlet fluid passageway, the resilient membrane further being positioned so that upon deformation of the encasement to flush the shunt, the membrane temporarily contacts the secondary valve seat in a manner to occlude the inlet fluid passageway.

28. A shunt as set forth in claim 21, including grommet means for non-adhesively attaching the bases to tubing means for channeling fluid to the inlet and from the outlet of the shunt.

29. A shunt as set forth in claim 21, including antechamber means for injecting medication into the shunt, the antechamber means having a relatively flexible encasement which defines an injection chamber, and a rigid needle shield situated within the injection chamber, wherein the needle shield includes needle stop means for preventing a tip of a needle from slipping off the needle shield during injection of medication into the injection chamber.

30. A shunt as set forth in claim 29, wherein the needle shield has a dog bone-like cross-section, and the ends of the needle shield are contoured to permit its abutment against the flexible encasement without occluding openings therethrough.

31. A flow control member for use with an implantable flow control valve for controlling the flow of fluid from one portion of the human body to another, the valve including a base invested within a valve housing, wherein the base forms a wall separating an inlet of the valve from an outlet of the valve, the base including at least one aperture therethrough for permitting flow of fluid through the valve from the inlet to the outlet, the flow control member comprising:

a rigid nail having an elongated shaft and an expanded head at an end of the shaft, the nail capable of being driven into the base and frictionally retained therein, or otherwise attached to the base, so that the head is suspended beyond the one side of the base; and a flexible resilient membrane positioned and retained on the shaft adjacent to the head, the membrane being generally arch-shaped and resiliently biased for contacting the base in a manner preventing fluid flow through the aperture from the inlet of the valve to the outlet of the valve.

32. A flow control member as set forth in claim 31, wherein the head is suspended beyond the outlet side of the base, and wherein the flexible resilient membrane is resiliently biased to normally contact the outlet side of the base generally along the outer edges of the membrane in a manner surrounding the aperture through the base and forming a releasable seal between the outlet side of the base and the outer edges of the membrane.

33. A flow control member as set forth in claim 32, wherein the membrane includes a central reinforced section which surrounds and is adjacent to the nail, and a peripheral flexible section which engages the base to form the seal therebetween.

34. A flow control member as set forth in claim 33, wherein the thickness of the peripheral flexible section of the resilient membrane can be adjusted to alter the releasable seal characteristics of the flow control valve.

35. A flow control member as set forth in claim 34, wherein the nail is heat welded to the base.

36. A method for assembling an implantable shunt system including a flow control valve for controlling the flow of fluid from one portion of the human body to another, the valve including at least one base invested within a valve housing and at least one flow control member, wherein the at least one base forms a wall separating an inlet of the valve from an outlet of the valve, the at least one base including at least one aperture therethrough for permitting flow of fluid through the valve from the inlet to the outlet, the steps comprising:

fixing the at least one flow control member to the at least one base in a manner permitting only controlled unidirectional fluid flow through the shunt;

attaching a first section of tubing to the at least one base by sliding an end of the first section of tubing into the base, placing a first tubing grommet into the end of the first tubing section to expand the end thereof, and then pulling the first section of tubing so the expanded end of the first tubing section engages the at least one base and forms a frictional attachment therewith;

attaching a second section of tubing to the at least one base by sliding an end of the second section of tubing into the base, placing a second tubing grommet into the end of the second tubing section to expand the end thereof, and then pulling the second section of tubing so the expanded end of the second tubing section engages the at least one base and forms a frictional attachment therewith, wherein the first and second sections of tubing, when so attached, define, in part, the inlet and outlet of the valve;

sliding the housing over the tubing to envelope the at least one base and adjacent sections of the first and second sections of tubing; and sealing the housing to respective adjacent portions of the first and second sections of tubing.

37. A method as set forth in claim 36, wherein the at least one base includes a first base defining a valve inlet fluid passageway, and a second base defining a valve outlet fluid passageway, the at least one flow control member including a first flow control member mounted to the first base, and a second flow control member mounted to the second base, and wherein the first section of tubing attaches to the first base and the second section of tubing attaches to the second base.

38. A method as set forth in claim 37, wherein the first flow control member is attached to the first base in a manner to normally permit free fluid flow through the inlet fluid passageway, but when the housing is deformed to flush the valve, the first flow control member is temporarily deformed to contact the first base in a manner to occlude the valve inlet fluid passageway.

39. A method as set forth in claim 37, wherein the second flow control member is attached to the second base to contact the second base in a manner normally occluding the outlet fluid passageway but selectively opening to permit controlled unidirectional flow therethrough.

40. A method as set forth in claim 37, wherein the first and second bases are spaced from one another within the housing to create, in connection with the housing, a flushing volume of fluid therebetween.

41. A method as set forth in claim 37, wherein each flow control member includes a rigid nail having an elongated shaft and an expanded head at an end of the shaft, and a flexible resilient membrane positioned and retained on the shaft adjacent to the head, the membrane being generally arch-shaped and wherein the membrane is fixed to the nail, and the nail is then press fit into its respective base until properly aligned, after which the nail is heat-welded to the respective base.

42. A method as set forth in claim 4!, wherein each base includes a rigid base outer housing and a valve membrane carrier, the valve membrane carrier being fixed to the rigid base outer housing after the rigid base outer housing is secured to the respective segment of tubing.

43. A method as set forth in claim 36, including the step of fixing a second end of the first tubing section to an antechamber.

44. A method as set forth in claim 43, including the steps of inserting a needle shield into the antechamber, and attaching a third section of tubing to the antechamber opposite the first section of tubing, to create a fluid flow pathway from the third section of tubing, through the antechamber, to the first section of tubing, and then through the valve to the second section of tubing.

* * * * *